United States Patent [19]

Bacon et al.

[11] Patent Number: 5,994,117
[45] Date of Patent: *Nov. 30, 1999

[54] **USE OF *BACILLUS SUBTILIS* AS AN ENDOPHYTE FOR THE CONTROL OF DISEASES CAUSED BY FUNGI**

[75] Inventors: Charles W. Bacon; Dorothy M. Hinton, both of Athens, Ga.

[73] Assignee: The United States of America as represented by the Department of Agriculture, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/580,664

[22] Filed: Dec. 29, 1995

[51] Int. Cl.⁶ .............................. C12N 1/20; C12N 1/00; C12N 1/12; C12N 1/14

[52] U.S. Cl. .............. 435/252.5; 435/32; 435/252.1; 435/252.31; 435/253.3; 435/254.7; 435/267; 435/822; 435/839; 424/93.4

[58] Field of Search .................. 424/93.4; 435/253.3, 435/32, 252.1, 252.5, 754.7, 252.31, 767, 822, 839

[56] References Cited

U.S. PATENT DOCUMENTS

| | | | |
|---|---|---|---|
| 4,588,584 | 5/1986 | Lumsden et al. | |
| 4,764,371 | 8/1988 | Pusey et al. | 424/93 |
| 5,416,672 | 5/1995 | Fahey et al. | 47/57.6 |
| 5,552,315 | 9/1996 | Slininger et al. | 435/253.4 |

FOREIGN PATENT DOCUMENTS

| | | | |
|---|---|---|---|
| 4205196 | 9/1992 | Germany | A01H 15/00 |

OTHER PUBLICATIONS

Pleban et al. European Journal of Plant Pathology 101(6): 665–672, Nov. 1995.
Butterworth et al. Journal of Applied Bacteriology 71: 484–496, 1991.
Farmer et al., J. Clin. Microbiol., 21 (1):46–76, Jan. 1985.
Wilson et al., Phytopathology 77:303–305, 1987.
Nelson et al., Plant Diseases 75(5):510–514, 1991.
Roberts et al. Lan. J. Microbiol. 38:1128–1134, 1992.
Hebbar et al. Sail Biology & Biochemistry 24(10):979–987, 1992.
Hinton and Bacon, "*Enterobacter cloacae* is an entophytic symbiont of corn", *Mycopathologia*, vol. 129, p. 117–125 (1995).
Lemanceau and Alabouvette, "Biological control of fusarium diseases by fluorescent Pseudomonas and non-–pathogenic fusarium", *Crop Protection*, vol. 10, pp. 279–286 (1991).
Bacon et al., "Scanning Electron Microscopy of *Fusarium moniliforme* within Asymptomatic Corn Kernels and Kernels Associated with Equine Leukoencephalomalacia", *Plant Disease*, vol. 76(2), pp. 144–148 (1992).
Norred et al., "Diffferential cyctoxicity and mycotoxin content among isolates of *Fusarium moniliforme*", *Mycopathologia*, vol. 115, pp. 37–43 (1991).
Gelderblom et al., "The cancer–initiating potential of the fumonisim B mycotoxins", *Carcinogenesis*, vol. 13(3), pp. 433–437 (1992).
Gelderblom et al., "Toxicity and carcinogenicity of the *Fasarium moniliforme* metabolite, fumonisin $B_1$, in rats", *Carcinogenesis*, vol. 12(7), pp. 1247–1251 (1991).
Raju et al., "An Asymbiotic Nitrogen–Fixing Bacterium from the Root Environment of Corn", *Proc. Nat. Acad. Sci*, vol. 69(11) pp. 3474–3478 (1972).
Norred et al., "Effectivenes of Ammonia Treatment in Detoxification of Fumonisin–Contaiminated Corn", *Fd. Chem. Toxic.*, vol. 29(12), pp. 815–819 (1991).
De Quattro, "Fungus and Bacterium: Alienated Intercellular Mates in Corn", ARS Press Release, distributed Oct. 1995.
Dialog (R) File 60: CRIS/USDA, "Identification and Development of Biocontrol Agents to Replace Seed Treatment Fungicides" CRIS Report, Jan. 1995.
Dialog (R) File 60: CRIS/USDA, "Formation and Toxicity of Metabolites of *Fusarium Moniliforme*", CRIS Report, Jan. 1995.

*Primary Examiner*—Frank C. Eisenschenk
*Assistant Examiner*—Mary K Zeman
*Attorney, Agent, or Firm*—M. Howard Silverstein; John D. Fado; Gail E. Poulos

[57] ABSTRACT

Agricultural methods of biological control and organisms useful in such methods are disclosed, such as novel endophytic symbiotic *Bacillus subtilis* and methods of biologically controlling fungal diseases of plants. These strains are useful vectors for the delivery of their beneficial gene products to plants.

5 Claims, 15 Drawing Sheets

USE OF *BACILLUS SUBTILIS* AS AN ENDOPHYTE FOR THE CONTROL OF DISEASES CAUSED BY FUNGI

BACKGROUND OF THE INVENTION

1. Field of the Invention

This invention relates to biological methods and products useful in agriculture. More specifically, the present invention is directed to a method for controlling diseases caused by *Fusarium moniliforme*, biological control agents useful in such a method, and biological agents useful in agriculture.

2. Description of the Prior Art

Fungi of the genus Fusarium are responsible for numerous crop plant diseases around the world. These fungi are particularly harmful to cereal crops, such as corn, sorghum, and wheat. For example, one or more species of Fusarium can be isolated in every season from nearly every vegetative or reproductive part of corn in every corn-growing region of the United States. A particular species of Fusarium can occur singly or as part of a complex of Fusarium species or fungi or other genera. Depending upon weather, soil and the particular cereal variety, damage to the crop can range from negligible to extensive. A common occurrence, for example, is for a Fusarium diseases caused by Fusarium fungi include seedling blight, root rot, stalk rot, and ear rot.

*Fusarium moniliforme* is the most widely prevalent and economically important Fusarium found on corn in the United States, and is the most frequently isolated Fusarium species in shelled corn. Seed lots with 100% infection are not uncommon. It is also the most frequent cause of ear rot, and has been implicated in seedling blight and root rot. One of the primary diseases affecting the corn crop in the United States is stalk rot, and *Fusarium moniliforme* is considered to be the predominant stalk rot fungus in at least 10 states: Florida, Idaho, Iowa, Minnesota, Nebraska, New Jersey, North Carolina, Pennsylvania, South Carolina, and Virginia. *F. moniliforme* is also known to produce a phytotoxin and at least five chemically distinct classes of mycotoxins.

*Fusarium graminearum* is found less often in corn kernels than *F. moniliforme*, primarily occurring in the humid sections of the corn belt east of the Mississippi River and along the Atlantic seaboard. *F. graminearum* is a cause of ear rot and seedling blight, and one of the important causes of stalk rot in the New England, Mid-Atlantic and Northern corn belt states. *F. graminearum* also produces mycotoxins in kernels and stalks.

Additional species of Fusarium fungi that are of lesser importance than *F. moniliforme* and *F. graminearum* in corn disease include *F. graminum, F. tricinctum, F. oxysporum*, and *F. soloni*. While these species are mainly of importance as parts of disease complexes, *F. tricinctum* has been reported to produce mycotoxins in kernels and stalks.

Most Fusarium fungi are not believed to be strong pathogens. Generally, they produce major symptoms and damage crops only when the crops are under stress. The advance of the fungi in the plant is determined largely by what stress is occurring and the rate of cell death in plant tissues. Fusarium fungi have a wide host range of cereals and grasses and very effective methods of survival in soil or plant residues. Wherever grasses or cereals are grown in the United States, Fusarium infection of seedlings, roots, stalks, or ears is always possible. Thus, a method of controlling Fusarium infection in cereal crops is highly desirable. See generally, Fusarium Diseases, Biology and Taxonomy (P. E. Nelson, T. A. Toussoun, and R. J. Cook, eds. 1981); Christensen and Wilcoxson (1966) Amer. Phytopathol. Soc. Monogr. No. 3, 59 p.; Koehler (1959) Illinois Agric. Exp. Stn. Bull. 658. 90 p.

Attempts have been made to control fungal infections of plants by biological means. For example, Kommedahl and Mew (Phytopathology, Vol. 65, 2396–300, 1975) have reported that three corn hybrids were coated with *Bacillus subtilis* and *Chaetomium globosum* to determine the effect on seedlings, final stands, stalk rot, and yields in the field, in comparison with the standard chemical seed treatment, captan. Stalk rot and breakage were less with the organism- and captan-coated seeds compared to non-coated seeds. Grain yields, however, were generally higher for the captan-coated seeds than for the organism-coated seeds. It was concluded that the organisms were not as consistent as captan in protecting the plants, and that additional research was required before the use of organisms for coating corn kernels would be commercially feasible. Kommedahl and Mew, supra, also reported that captan is widely used as a seed treatment because it is reliable, easy to apply, and inexpensive. It was also reported, however, that captan is not always a good seed treatment under all conditions. In particular, Kommedahl and Mew, supra, reported that under prolonged conditions of low soil temperature and high soil moisture, biological controls proved superior to captan in reducing root infections. This was attributed to the possible multiplication of organisms and their growth from the seed to the root surface. For additional discussion of biological control of fungal infections in plants see generally: R. J. Cook, BIOLOGICAL CONTROL OF PLANT PATHOGENS (Amer. Phytopathol. Soc. 1982); Burges, H. D. (ed.) (1981) Microbial Control of Pests and Plant Disease 1970–1980, Academic Press, New York; Baker, Phytopathology Vol. 58, 1395–1401; Kommedahl and Chang, (1966), Phytopathology Vol. 56, 885; Kommedahl, (1972) Plant Dis. Rep. Vol. 56, 861–863; Mitchell, (1973) Soil Biol. Biochem. Vol. 5, 721–728; Papavizas, (1973) Soil Biol. Biochem, Vol. 5, 709–720.

Kawamoto and Lorbeer (Plant Dis. Reptr., Vol. 60, 189–191, 1976) report that onion seedlings were protected from damping off, caused by a particular strain of *Fusarium oxysporum* by infesting the onion seedlings with *Pseudomonas cepacia* Burkh strain 64-22. This *P. cepacia* strain (64-22) was reported to be recovered from the root, root-stem zone and seed coat on 18-day old seedlings from inoculated seeds. Live cells of *P. cepacia*, 64-22 were reported to inhibit *Fusarium oxysporum* f. sp. *cepae*, while dead cells and culture filtrate did not. The authors stated that the mechanism through which *P. cepacia* protects young seedlings was open to speculation. The authors concluded that the experiments reported at least supported the feasibility of biological control measures to improve onion seedling stand, but that "at present we could not recommend infesting onion seed with *P. cepacia* for commercial plantings . . . ", presumably because some strains of *P. cepacia* have been reputed to be pathogenic to onions.

R. D. Lumsden (Phytopathology Vol. 72, 709, 1982) reported that a strain of *P. cepacia* is antagonistic to *Pythium aphanidermatum* and protects cucumber seedlings from infection by this fungus in soil. In U.S. Pat. No. 4,588,584, to Lumsden et al, a new biotype of *P. cepacia* designated SDL-POP-S-1 is described as protecting cucumber and peas from Pythium disease. Protection is afforded through bacterial inoculation of seeds.

Another strain of *Pseudomonas cepacia* protected Chinese Aster against wilt caused by *Fusarium oxysporum* f. sp. *callistephi* in greenhouse and field tests (Cavileer et al, American Phytopathological Society Annual Meeting, Abstract No. 522, 1985).

One isolate of *Enterobacter cloacae*, *E. cloacae* EcET-501, in addition to its ability to fix nitrogen, has been shown to have biocontrol potential for Fusarium wilt of cucumber (Sneh et al, Phytopathology, Vol. 74, 115–1124, 1984), Phythium blight of turfgrass (Nelson et al, Phytopathology, Vol. 82, 206–210, 1992), Sclerotinia dollar spot of turf (Nelson et al, Plant Dis., Vol. 75, 510–514, 1991), Pythium seed rot of vegetables (Chao et al, Phytopathology, Vol. 76, 60–65, 1986; Hadar et al, Phytopathology, Vol. 73, 1322–1325, 1983; Nelson et al, Phytopathology, Vol. 76, 327–335, 1986), and some postharvest diseases of fruit (Wilson et al, Phytopathology, Vol. 77, 303–305, 1987; Wilson et al, Plant Dis., Vol. 69, 375–378, 1985). In addition to Phythium species, this *E. cloacae* is also effective in suppressing species of Fusarium and Rhizopus in the soil (Wilson et al, Phytopathology, Vol. 77, 303–305, 1987; Campbell, Biological Control of Microbial Plant Pathogens, New York: Cambridge University Press, 1989).

U.S. Pat. No. 4,588,584 (Lumsden et al, 1986) discloses that a variety of bacterial strains including members of the genera Pseudomonas, Bacillus, and Enterobacter were found to be antagonists of Fusarium. Among the fungal antagonists, root-colonizing Pseudomonads, *P. fluorescens* and nonfluorescent *P. cepacia* were the most numerous. The patent also discloses that *Enterobacter cloacae* was a medium to poor colonizer.

While various biocontrol agents for control of pathogenic fungi are known in the art, there still remains a need for an effective biocontrol agent for pathogenic fungi, especially Fusarium, and especially a biocontrol agent which is a symbiotic endophyte. The present invention described below is an endophytic symbiont and is antagonistic to pathogenic fungi. The present invention provides a method for controlling pathogenic fungi in agricultural crops which is different from the prior art biocontrol agents.

SUMMARY OF THE INVENTION

It is, therefore, an object of the present invention to provide biocontrol agents for the control of pathogenic fungi in plants.

It is another object of the present invention to provide a method for biocontrol of fungal infection in plants.

Another object of the present invention is to provide methods of inoculating plants as well as bacterial strains useful in such methods, which protect plants from fungal infection and thereby enhance plant yields.

A further object of the present invention is to provide a bacteria which is an endophytic symbiont and can serve as a vector for the introduction to the plant of beneficial gene products produced by the bacterium.

A still further object of the present invention is to provide a *Bacillus subtilis* which is an endophytic symbiont which can serve as a vector for the introduction to the plant of beneficial gene products produced by the bacterium.

Another object of the present invention is to provide seeds coated with an agricultural inoculum containing an endophytic symbiont of *Bacillus subtilis*.

Further objects and advantages of the present invention will become apparent from following description.

Deposit of the Microorganism

*Bacillus subtilis*, designated RRC 101, has been deposited under the provisions of the Budapest Treaty with the American Type Tissue Culture Collection (10801 University Boulevard, Manassas, Va. 20110-2209 USA) on Dec. 14, 1995. The Accession number is ATCC 55732.

DETAILED DESCRIPTION OF THE INVENTION

Figure 1A:
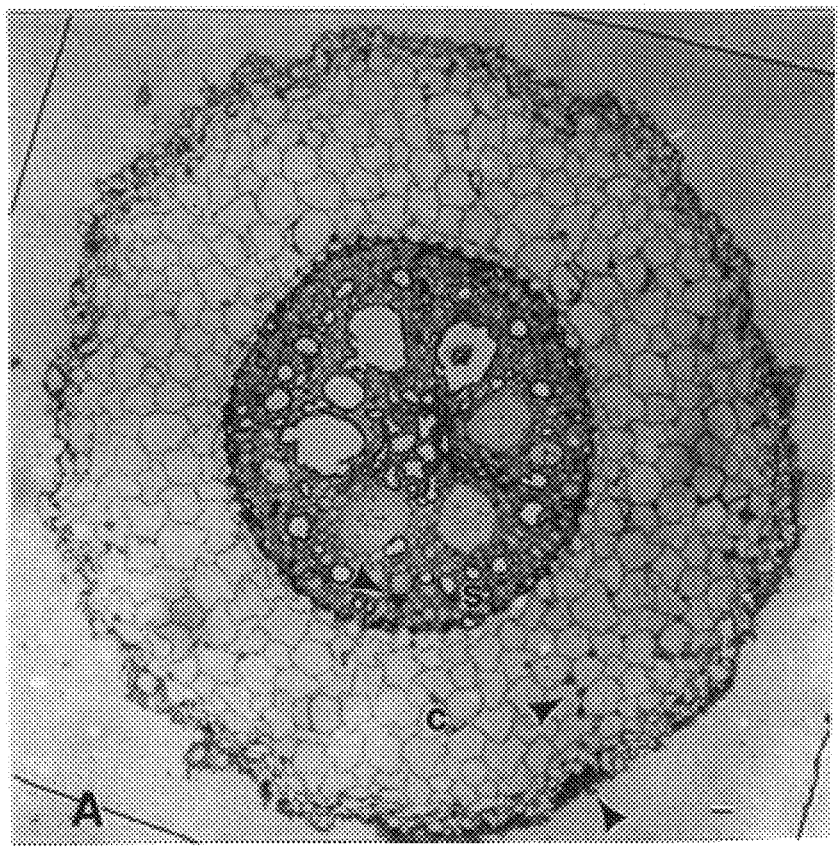
FIGS. 1a–1d are phase-contrast micrographs of a primary root of the Italian corn cultivar infected with *Bacillus subtilus*. 1a is a cross section of the root taken near the tip showing its organization into epidermis with bacteria at arrow, moving inward to the cortex, c, showing bacteria at arrow, and finally into the stele, s, with bacteria at arrow just within the endodermis; bar 100 μm. 1b is a section of 1a enlarged to show bacteria, arrow, located over the epidermis, e, and bacteria located within the intercellular spaces of the cortex, c, showing the intercellular location of the bacterial cells, arrows, bar, 10 μm. 1d is of cells of the stele enlarged X1000 under oil showing the bacteria at arrow next to primary phloem cells, p, just below the endodermis, en; bar, 10 um.

The finding that *Bacillus subtilis* is biologically associated with corn roots establishes it as an important organism for biocontrol of corn seedling diseases.

While biocontrol of corn pathogens with bacteria has potential (Campbell, Biological Control of Microbial Plant Pathogens, New York: Cambridge University Press, 1989), a suitable bacterium has not been reported which might control the major pathogens of this grass, particularly those fungi which coexist in corn plants as symptomless endophytes. The biocontrol of one pathogen, *Fusarium moniliforme Sheldon*, is highly desirable not only because of the damage done to corn (Kommedahl et al, Fusarium: diseases, biology and taxonomy, University Park: The Pennsylvania State University Press, 94–103, 1981) but also because this fungus, as a symptomless endophyte, produces several mycotoxins on corn (Bacon et al, Appl. Environ. Microbiol., Vol. 78, 302–305, 1989; Bezuidenhout et al, J. Chem. Soc., Chem Commun. 1988, 743–745; Gelderblom et al, Carcinogenesis, Vol. 7, 1899–1901, 1986), and is associated with several human and animal toxicoses of unknown etiology (Colvin et al, Mycopathologia, Vol. 117, 79–82, 1992; Gelderblom et al, Carcinogenesis, Vol. 9, 1405–1409, 1988; Marasas et al, Toxigenic Fusarium species, University Park: The Pennsylvania State University Press, 1984; Norred et al, Food Chem. Toxicol., Vol. 28, 89–94, 1990; Wang et al, J. Biol. Chem., Vol. 266, 14486–14490, 1991). The control of this fungus by fungicides applied to kernels, while effective in preventing soil-borne inoculum of this fungus from infecting corn roots, would be ineffective in preventing infections produced by the systemic seed-borne hyphae of this pathogen. Seed lots of corn maybe infected with *F. moniliforme* by as much as 90% (Kommedahl et al, supra), and much of this infection occurs systemically which plays an important part in infecting seedlings (Bacon et al, supra) and the accumulation of toxins within kernels, especially the fumonisins (Bacon et al, Plant Dis., Vol. 72, 144–148, 1992).

During routine screening of corn cultivars for resistance to seedling infection by *Fusarium moniliforme* and for any microorganisms associated with this resistance, it was found that a *B. subtilis* was associated with the roots of a *Fusarium moniliforme*-negative unknown cultivar of corn obtained from Italy. This heretofore unknown endophytic habit expands the utility of *B. subtilis*, RRC 101 as a biocontrol agent which is now primarily used as a seed protectant.

Rifampicin-resistant mutants of RRC 101 were isolated from nutrient agar containing 100 micrograms of rifampicin per milliliter (Campeau et al, Applied and Environmental Microbiology, vol. 54, 2432–2438, 1988 which is herein incorporated by reference). Two strains, designated Ent2655 and Ent24WF, were identical to RRC 101. Strain Ent24WF mutant produces a more pronounced inhibitory effect on the growth of *F. moniliforme* and other fungi either cultured in vitro. Resistance to the antibiotic rifampicin is rare among soil and plant bacteria. The chromosomal nature of the mutation affords greater stability than occurs with plasmid-borne markers and it is not easily transferable. Thus, mutations to this antibiotic also can be used to study the ecological success of parent types on live soils and in the in planta situation.

The method of this invention is applicable to any plant whether cultivated or wild and particularly to grasses, especially corn. The bacterium of the present invention can colonize seedlings at a variety of soil temperatures. Seedlings can be infected at about 75° F. and lower, down to about 35° F. Temperatures lower than this prevents corn germination; the bacterium, however, survives even this low temperature. The bacterium of the present invention can take desiccation for at least two years on corn kernels and still remain infective. Further, RRC 101 and it's rifampicin mutants can be frozen (0° C.) in the soil and readily recovered after a one year period.

RRC 101 and it's rifampicin mutants infect seedlings during the germination stage through scars and damaged roots produced during the germination process. There is no need to inject the bacterium as is commonly done for other biological control bacteria. The bacteria in aqueous solution can be sprayed directly onto seeds. The seeds are allowed to dry overnight at room temperature. The concentration of bacteria in a sprayable aqueous solution is approximately about $10^3$ to about $10^9$ bacteria per milliliter of water. The seeds can be stored at about 4° C. to about 25° C. for at least about 12 months prior to planting. When the seeds are planted, the bacteria infects the seedlings from this initial topical application.

RRC 101 and it's rifampicin mutants can inhibit naturally fungus-contaminated corn kernels allowing at least about a 70–90% germination of kernels. These same kernels will germinate only 43–50% without the topical application of RRC 101 and it's rifampicin mutants. The target pathogens include plant pathogenic fungi, especially species of Fusarium, Aspergillus, and Pythium; more specifically, for example, *Aspergillus fumigatus, Aspergillus parasiticus, Fusarium proliferatum, Fusarium graminearum,* and *Fusarium subglutinans*. These fungi are pathogenic to corn, wheat, barley, and other plants as well as known producers of potent mycotoxins on corn. Germination in soils with RRC 101 and it's rifampicin mutants and fungus (*F. moniliforme*) results in complete protection of corn even when the most virulent isolate of the fungus was used. Thus, protection is obtained under soil conditions. In both green house conditions and field conditions, no disease is produced by RRC 101 and it's rifampicin mutants. During the growing season, RRC 101 and it's rifampicin mutants was distributed throughout the plant including stems leaves, and roots but was not recovered from kernels.

The following examples are intended only to further illustrate the invention are not intended to limit the scope of the invention as defined by the claims.

EXAMPLE 1

Bacteria Isolation and Identification

Corn kernels used for isolation of the bacteria were of an unknown cultivar obtained from Italy. The kernels were surface sterilized by shaking for 10 minutes in full strength Clorox bleach, 5.25% sodium hypochlorite, rinsed three times in sterile water, and germinated at room temperature in either deep glass culture dishes (7.5×10 cm) or standard Petri dishes containing Difco potato dextrose agar (PDA) under a 12 hour light-dark cycle provided by fluorescent lights. Kernels showing fungal infection were discarded and only kernels free of fungi were used as a source for bacterial isolations. Isolations of bacteria were made either directly from the rhizoplane of aerial roots of seedlings or from colonies produced directly on the PDA where roots made contact. All isolated bacteria were maintained and cultured on DIFCO BACTO nutrient agar for 5 to 7 days or nutrient broth for 1 to 2 days at 31° C. before being used for identification. Bacterial isolates were identified by their cellular fatty acid profiles (Microbial Identification System, 115 Barksdale Professional Center, Newark, Del. 19711) and diagnostic biochemical tests conducted at 37° C. (Micro-ID, Durham, N.C.) as disclosed in Bacon et al, Plant Dis., Vol. 76, 144–148, 1992; Ewing, Identification of Enterobacteriaceae, New York: Elsevier, 381–390, 1986; Farmer et al, J. Clin. Microbiol., Vol. 21, 46–76, 1985; all herein incorporated by reference. The bacterial isolates were stored on filter paper or silica gel at −20° C.

The cellular fatty acid profiles indicated that all bacteria isolated from the roots of the Italian corn cultivar were

*Enterobacter cloacae*. The bacterium was a Gram-negative rod and was further characterized by being positive for the Voges-Proskauer reaction, nitrate reductase, ornithine decarboxylase, and β-galactosidase. This bacterium also fermented arabinose and malonate. It was negative for phenylalanine deaminase, lysine decarboxylase, urease, $H_2S$, and indole production. Further, it lacked the ability to utilize adonitol, inositol, and sorbitol and to hydrolyze esculin. These biochemical characteristics and the fatty acid profiles placed this bacterium in the family Enterobacteriaceae, the tribe Klebsielleae as *E. cloacae* (Ewing, supra; Farmer et al, supra). This original isolate of *B. subtilus* is designated RRC 101.

EXAMPLE 2

Seed Inoculations

Corn kernels were subjected to a double sterilization process in which kernels were surfaced sterilized as described above in Example 1, and then subjected to a mild heat treatment (Bacon et al, Plant Dis., Vol. 78, 302–305, 1994, herein incorporated by reference) to remove both external and internal bacteria and fungi. This process produced sterile seedlings up to the 3 leaf stage of growth that remained so during the study. Sterile kernels were inoculated with bacteria and seedlings were grown for 3 to 6 weeks aseptically in culture tubes, 20×30 cm, containing sterile soil, in a plant growth room under 16 hours of light (an average of 256 uE $m^{-2}$ $s^{-1}$ at 21–26° C.). The corn cultivar, yellow field corn Trucker's Favorite, and an inbred dent line, Yellow Proudfit (PR), were used. The isolates of *B. subtilis* used to inoculate kernels were cultured at 30° C. in nutrient broth or on nutrient agar for 24 hours and 0.01 ml ($4 \times 10^6$ cfu/ml) was inoculated onto sterilized kernels that were then grown for 7 to 10 days in glass culture vessels on either PDA, damp filter paper, or sterile soil. Controls consisted of double sterilized corn kernels germinated on their respective media or filter paper. All kernels germinated and roots from germinated seedlings were aseptically removed and subjected to microscopic examination for comparison with the natural infections observed in the Italian corn cultivar. Roots were also plated on nutrient agar and the isolated bacterium biochemically identified as described above. Uninoculated, double sterilized kernels and seedlings grown from these were free of bacteria when used as controls.

Figure 1B:
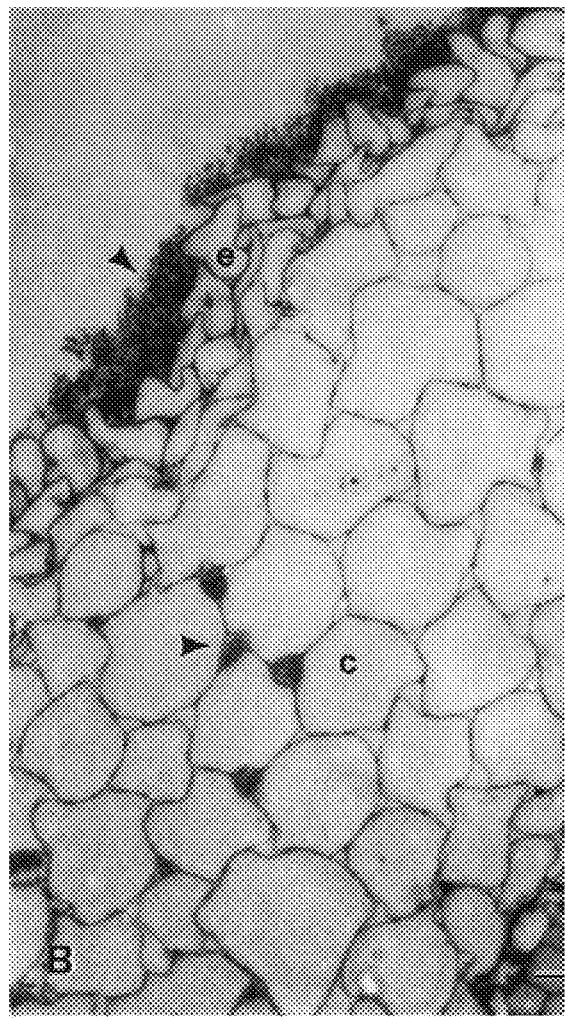
Figure 1C:
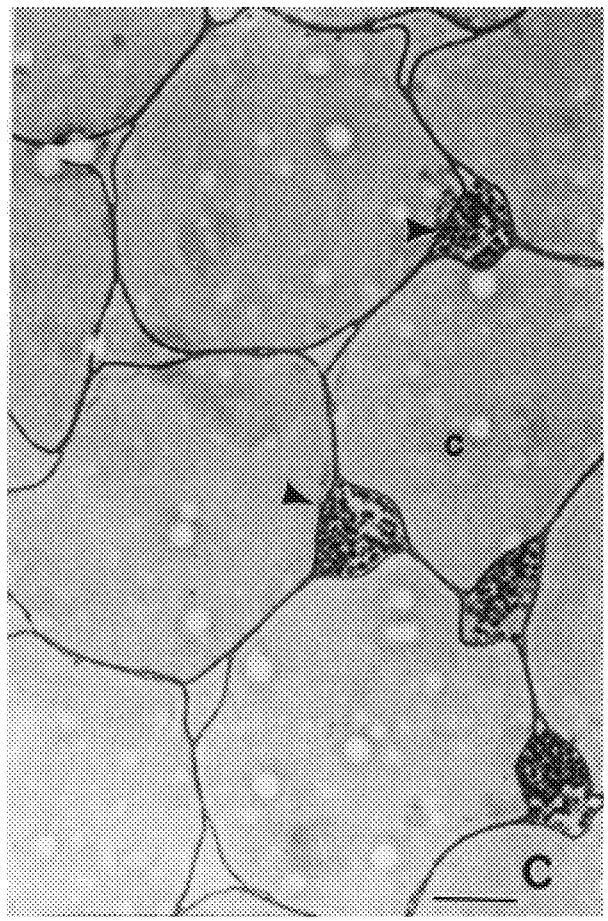
Figure 1D:
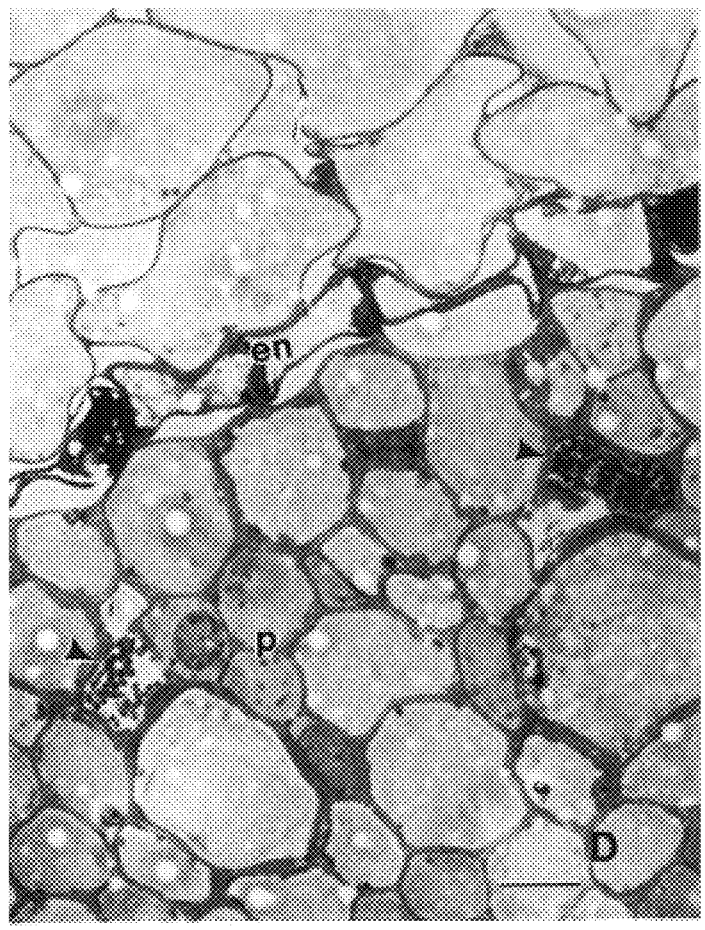

Bacteria were observed on the rhizoplane of seedling roots grown on media or filter paper. When sections of these roots were examined microscopically, bacterial cells were also observed internally (FIG. 1a). On corn germinated in culture dishes, the bacteria were distributed uniformly over the epidermis (FIG. 1b), and randomly distributed intercellularly in several locations of the cortex (FIGS. 1b and 1c). No bacterial cells were observed within the endodermis, but bacteria were observed intercellularly within the outer margin of the pericycle, usually adjacent to phloem cells (FIG. 1d). They were not observed among cells of the pith area. In no instance was there any evidence of damage to host cells, and cells of this bacterium were completely intercellular (FIG. 1c). The presence of *B. subtilis* in leaves and stems of one to six-week-old seedlings were indicated by its isolation from these surface sterilized plant parts.

Figure 2A:
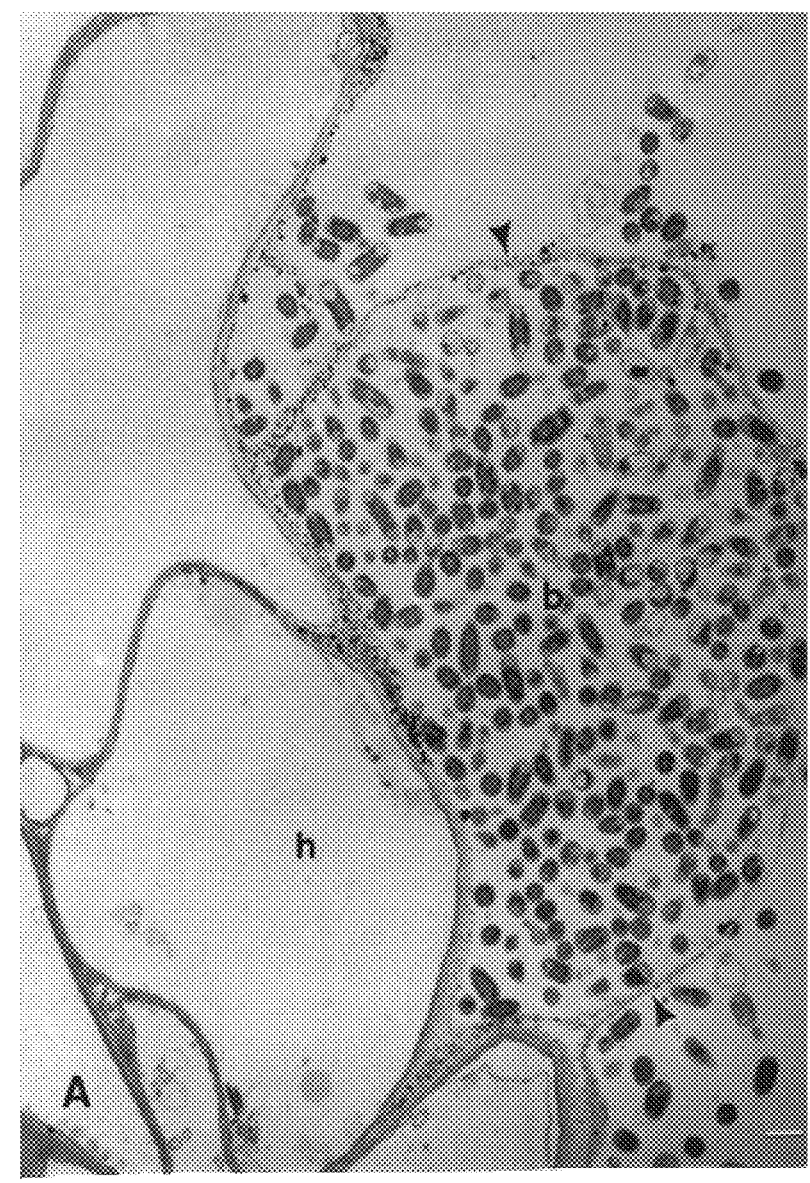
FIGS. 2a–2d are transmission electron micrographs of corn roots infected with *Bacillus subtilis*. 2a is a cross-section of a primary root showing the appearance of bacterial cells over the epidermis, h, and a dense number of bacterial cells, b, being covered by a matrix-like material external to the epidermis (delimited by arrows), X4,640. 2b is a root infection showing bacteria between the intercellular spaces formed by three adjacent cells, h, observed in the Italian cultivar, X7,250. 2c shows several intercellular spaces containing bacterial cells, X3,375. 2d shows symbiotic similarity of root infection by *B. subtilis* when the bacterium was inoculated onto kernels of Trucker's Favorite. Bars represent 1 μm for all panels.
Figure 2B:
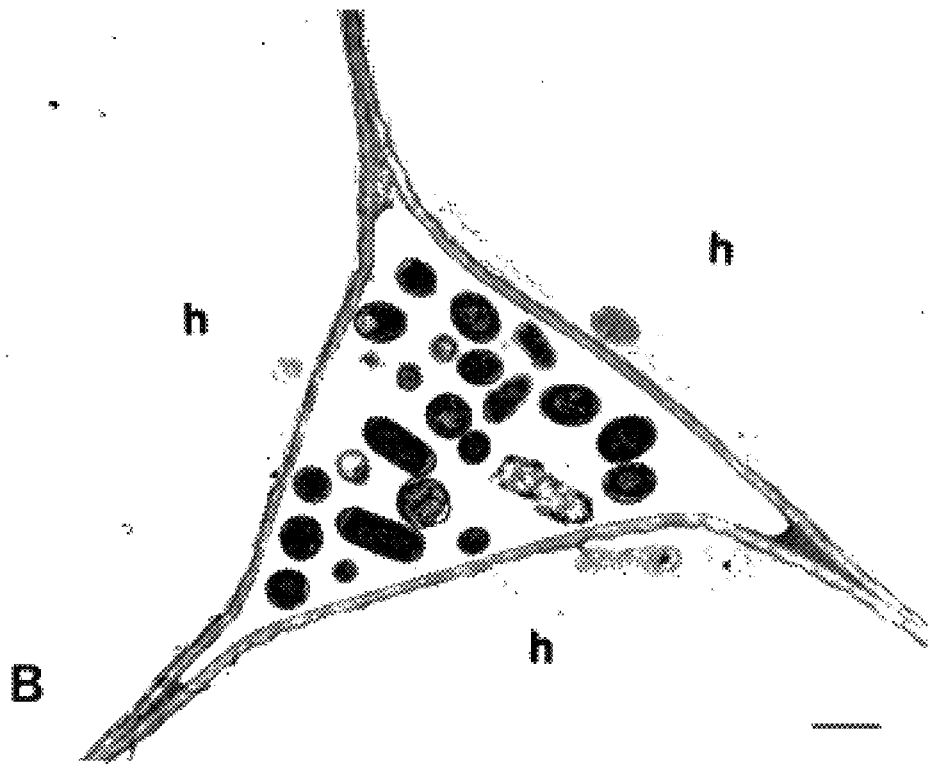
Figure 2C:
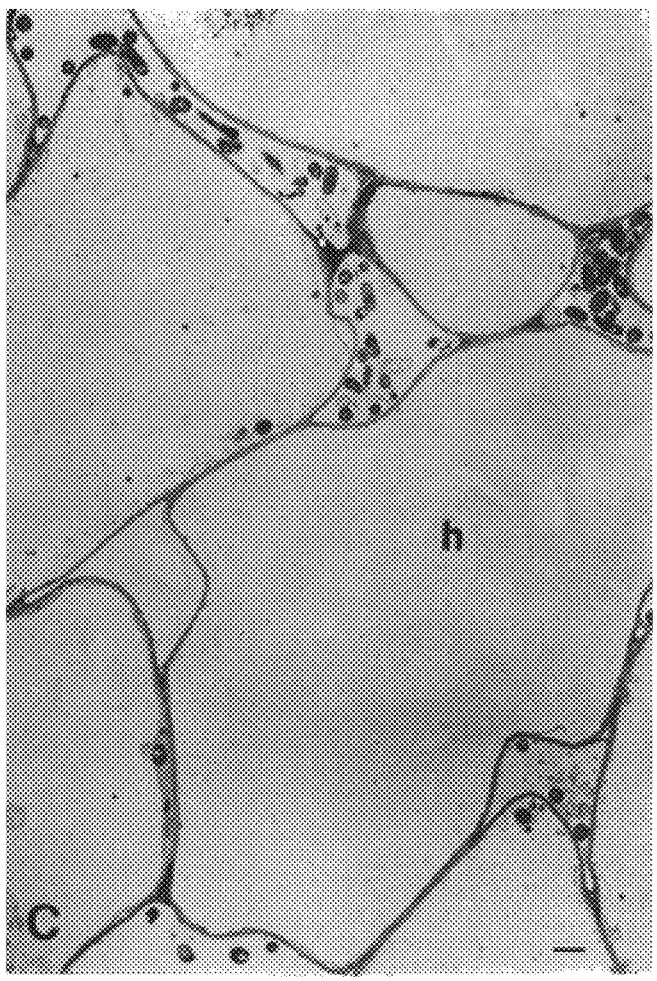
Figure 2D:
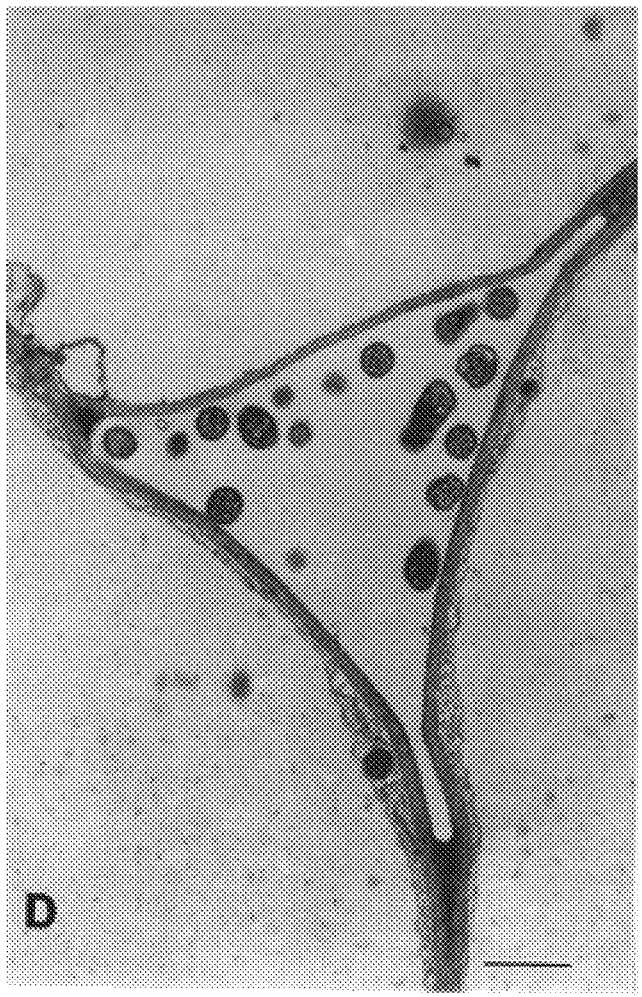
Figure 3A:
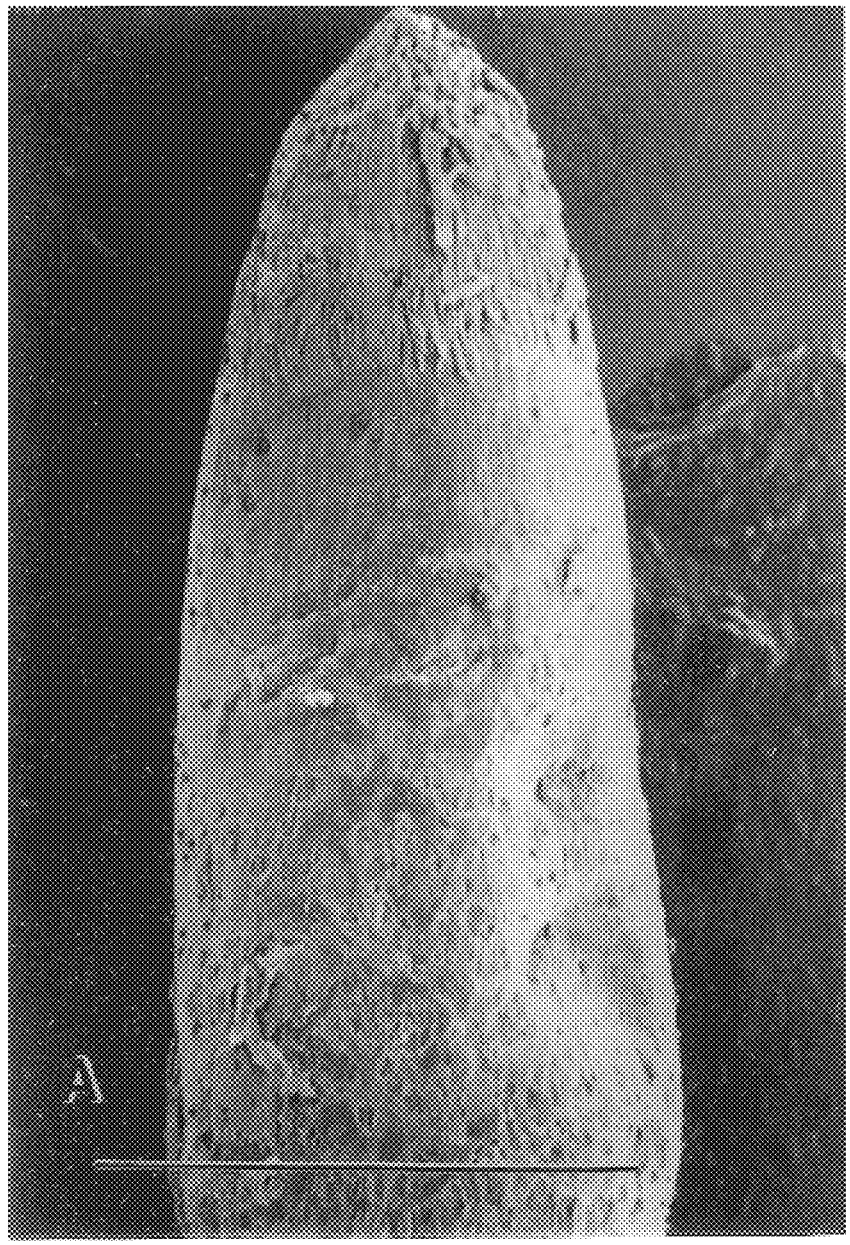
FIGS. 3a–3b are scanning electron micrographs of a primary corn root tip infected with *Bacillus subtilis*. 3a is a section of the root tip examined for the distribution of the bacterium along the external root surface; bar, 1 mm. 3b is a magnified section of 3a showing the bacteria along the external root surface, and the presence of the matrix-like material (m) covering the cells observed in FIG. 2a; bar 10 μm.
Figure 3B:
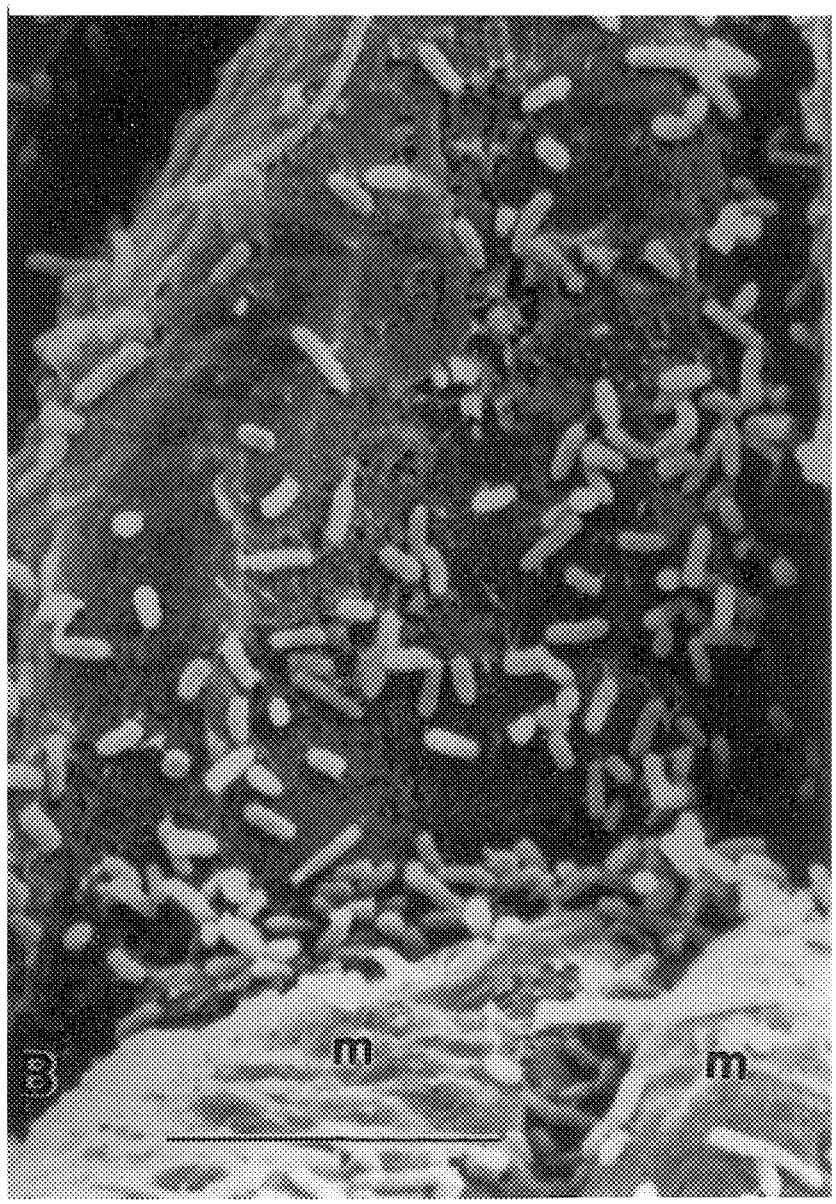
Figure 4A:
FIGS. 4a–4d are scanning electron micrographs of a *Bacillus subtilis*-inoculated Trucker's Favorite corn kernel germinating. 4a is a two to four day-old kernel showing the rupture produced prior to germination. 4b is an enlarged magnification of the kernel in 4a showing the bacteria (arrow) on the endosperm below the pericarp. 4c is enlarged view of 4a showing bacteria (arrows) on the pericarp. 4d is enlarged view of 4a showing bacteria (arrows) on the starchy endosperm.
Figure 4B:
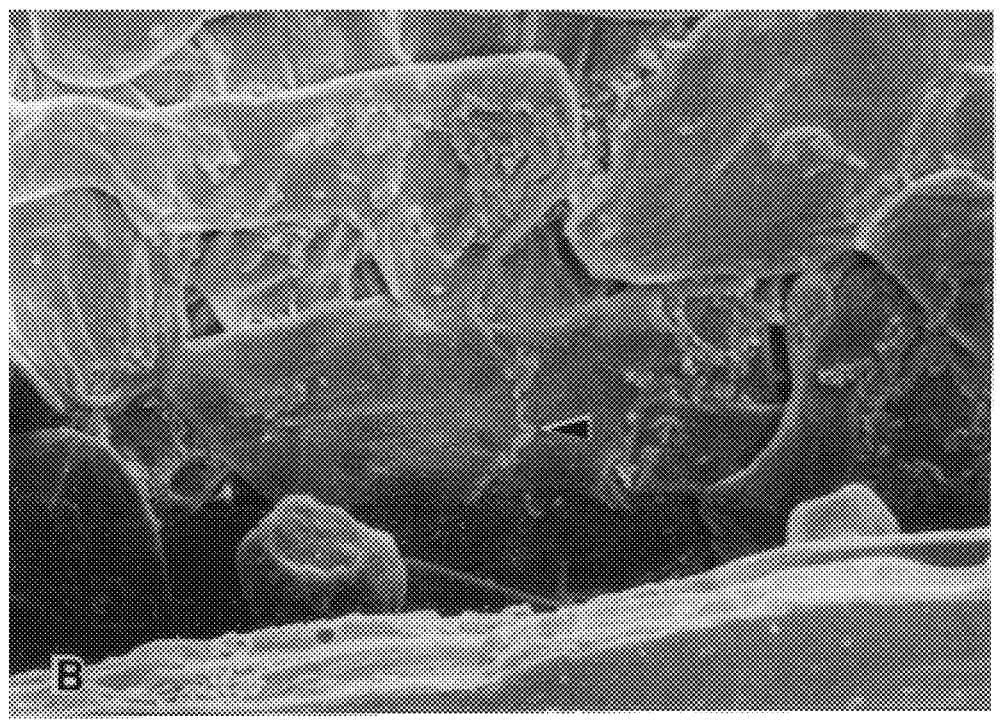
Figure 4C:
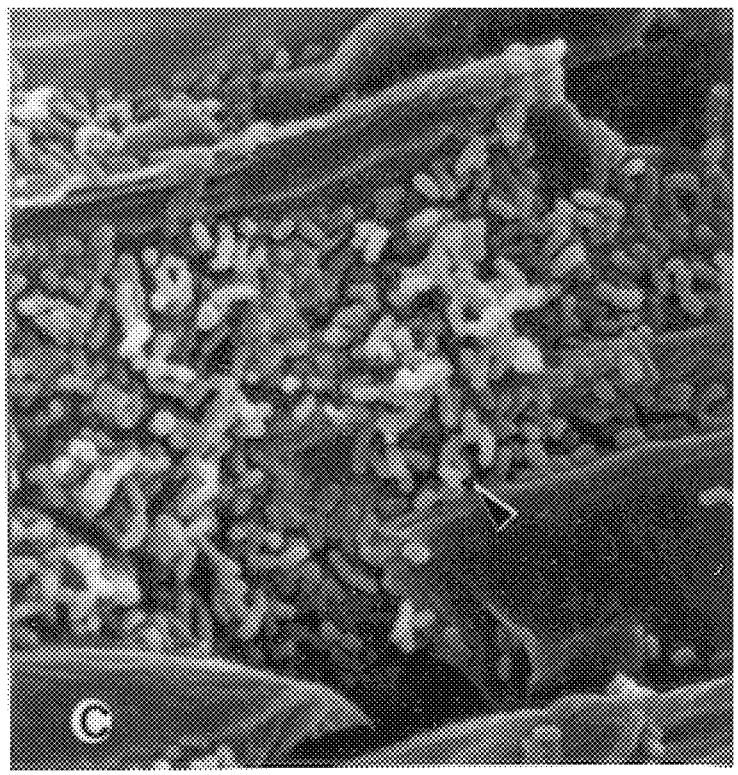
Figure 4D:
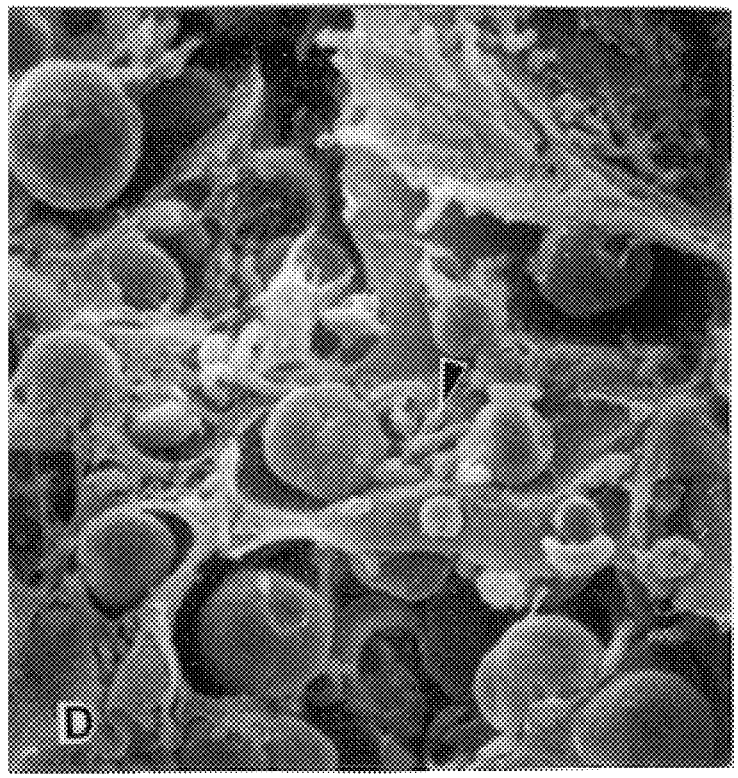

There was no evidence at the ultrastructural level of pathological damage to cells of the endodermis and stele nor were any bacteria observed within cells. A matrix-like capsule was observed surrounding the bacterial cells located on the external surface of the primary foot (FIG. 2a). The intercellular nature of this bacterium was clearly demonstrated at the ultrastructural level (FIG. 2b). There is a proliferation of bacterial cells within the intercellular spaces, particularly those that were connected (FIG. 1c and FIG. 2c). The identical intercellular nature of this bacterium was observed in the field corn cultivar, Trucker's Favorite (FIG. 2d) and the inbred line PR (data not shown), the two cultivars inoculated with this bacterium. Scanning microscopy established that *B. subtilis* was also distributed externally along both the secondary and primary seedling roots of Trucker's Favorite as well as the root cap of the primary root (FIGS. 3a and 3b). The application of bacteria to the pericarp of surface sterilized kernels resulted in seedling root infection of both cultivars. Scanning electron microscopy established that *B. subtilis* had colonized the endosperm of germinating kernels (FIGS. 4a,b,c, and d). The bacteria apparently migrated through the germination slit (FIG. 4a) formed early in germination and onto the starchy endosperm (FIG. 4d). The bacteria did not interfere with the percentage germination nor emergence and time of emergence of the radicle and coleoptile.

EXAMPLE 3

Bacteria-Fungus Antagonism

Figure 5:
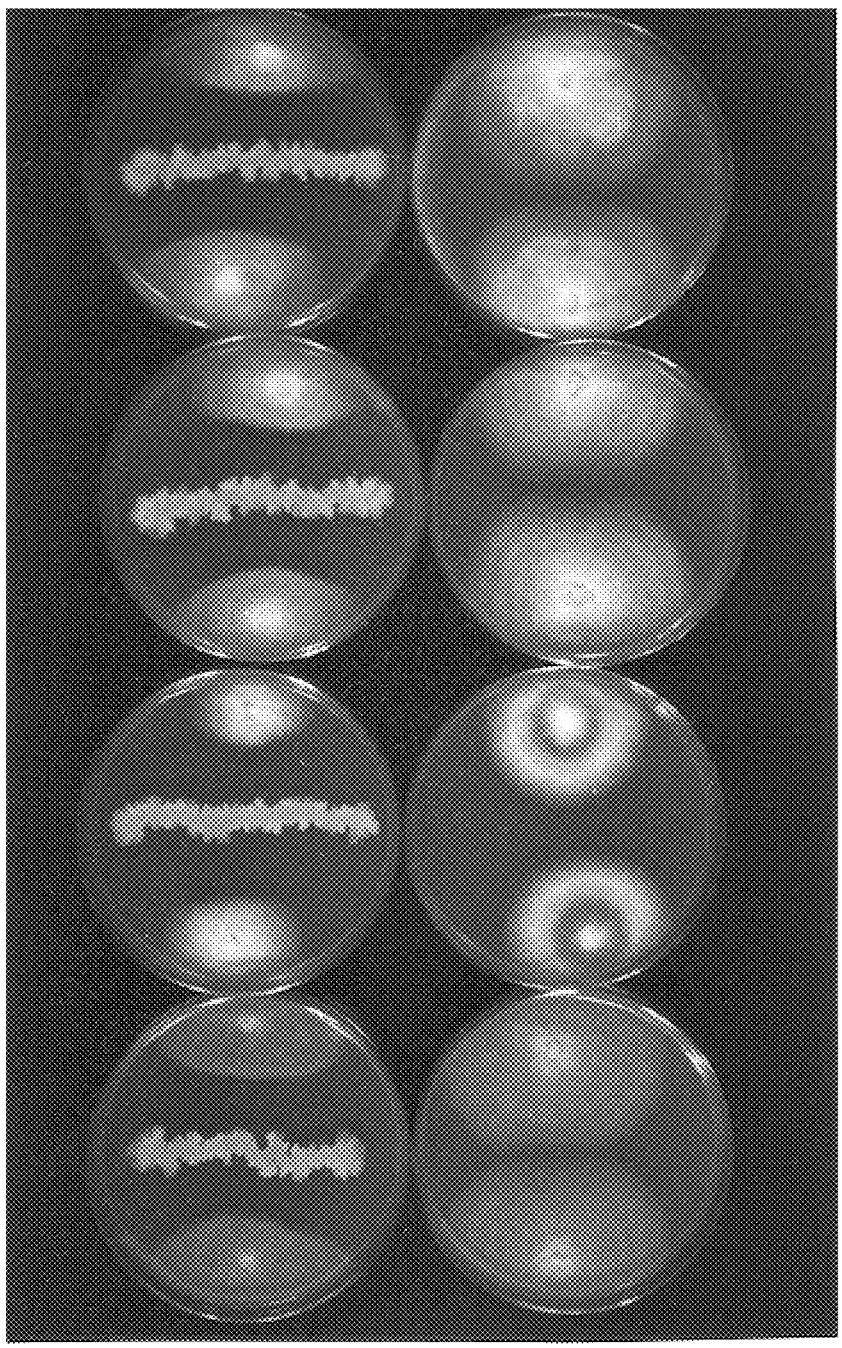
FIG. 5 is a photograph showing antagonism between *Bacillus subtilis* and four isolates of *Fusarium moniliforme* on nutrient agar. Columns (a) and (b), fungus control and bacterial treatment groups, respectively. The fungal strains are from top to bottom MRC 826, RRC 410, RRC 408, and RRC 374.

Inhibitory studies between the bacterium and fungi were conducted on either nutrient agar or PDA. The isolates of *F. moniliforme* used were RRC 374, RRC 408, RRC 410, and MRC 826. All these fungi were isolated from corn except RRC 410 which was isolated from rice. These isolates were rated as poor to strong pathogens of corn seedlings according to the corn seedling test (Bacon, Plant is., Vol. 78, 302–305, 1994). The two other toxic species of fungi used were *Aspergillus flavus* and *A. parasiticus*. The fungi were grown on PDA for three to seven days, two mycelial plugs removed form the outer margins of each fungal species, and two plugs placed opposite each other on the outer margin of a fresh agar plate of either nutrient agar or PDA. The bacteria used for these experiments were grown on nutrient agar for two to three days and one inoculation loop streaked down the center of each plate between each fungal agar plug of each plate immediately after inoculation with the fungal plugs (FIG. 5). Control plates consisted of fungi or bacteria placed on plates alone or as described above but without the bacteria. The plates were incubated in the dark at 25 to 27° C., until the fungi on the control plates had grown together.

The growth of all three fungi on both media were held in check. This inhibitory property of the bacteria was effective to all isolates of *F. moniliforme* which possessed different growth rates on media and pathogenicity to cultivars of corn seedlings (FIG. 5).

The antagonistic effect of RRC 101 on *Aspergillus fumigatus, Aspergillus parasiticus, Fusaium proliferatum, Fusarium graminearum, Fusaium subglutinans, Diplodia zeae, Colletotrichum graminicola, Clasosporium herbarum, Alternaria alternata, Penixillium chrysogeum*, Pythium sp., and *Rhizoctonia solani* was tested as described above using the agar disk assay. *B. subtilis* controlled the growth of all of these fungi as well.

EXAMPLE 4

Microscopy and Bacterial Distribution

Seedling roots used for microscopy were aseptically cut into 1.0 mm sections and fixed in 4% glutaraldehyde containing 0.1 M sodium cacodylate buffer for 24 hours. The tissue was rinsed in 0.1 M sodium cacodylate twice, 5 minutes each and postfixed 2 hours in 2% osmium tetroxide containing 0.1 M sodium cacodylate buffer. The tissue was rinsed with buffer, dehydrated in an ethanol series of 30%, 50%, 70%, 90%, and 100% (ethanol was diluted with distilled water) and embedded in Spurr's resin. A Reichert ultramicrotome was used to cut epoxy embedded samples. Samples used for examination with the light microscope were cut into 0.5 µm thick sections, stained with Azure II, and examined with phase-contrast filters on a Zeiss light microscope. Samples (0.1 µm thick) used for transmission electron microscopy were stained with uranyl acetate and lead citrate and examined with a JEOL 100II transmission electron microscope. Samples prepared for scanning electron microscopy were processed as described above except after the dehydration sequence, they were critical point dried, mounted on specimen holders, sputter coated with gold-palladium in an Anatech Ltd. Hummer X Sputter Coater and examined using a Phillips 505T scanning electron microscope.

The distribution of bacteria within the above ground portions of plants were determined by aseptically culturing corn seedlings produced from double sterilized kernels. The seedlings were grown for one to sixteen weeks in the light room as described above for bacterial inoculations. The cultivars Reid Yellow Dent and Silver Queen were grown in pot culture in the greenhouse from June to August, as well as in a light room. Seeds were double sterilized as above and inoculated with RRC 101 or its Rifampicin mutants, Ent24wf and Ent26ss. Kernels were planted in sterilized soil mix 3B-MIX, watered and fertilized as needed. Plants parts were removed, surface sterilized in full strength bleach (5.25% sodium hypochlorite) for 15 minutes and plated out on nutrient agar. Plants were also removed and measured for either dry weight of shoots, roots, or length of roots and shoots (Table 1 below). Leaf widths were also determined (Table 2 below). All isolated bacteria were biochemically characterized, as described above, to confirm its identity. The controls, which consisted of uninoculated double sterilized kernels germinated and grown as described for the treatment groups, did not yield bacterial colonies when their leaves and stems were surfaced sterilized and plated on nutrient agar. In no instance during the growth and maturation period of corn was there any indication of a reduction in growth. There were no observable destruction of leaves, stems, or roots in the bacterial infected plants, macroscopically or microscopically as shown in FIGS. 1–4.

The strain of the present invention is a natural symbiotic bacterium which also can be readily transferred to at least two corn cultivars as an endophyte. Its colonization and endophytic distribution within corn stem and leaf tissues of all young plants examined suggest that an infected plant might remain infected until plant maturity and kernel development.

Bacterial-infected corn seedlings and their roots showed no evidence of disease during a sixteen-week observation period and indeed show enhanced growth over controls (See Tables 1–4). Bacteria-inoculated corn germinated and when the resulting seedlings were grown on sterile filter paper, identical distribution and location of bacteria were observed as those on the medium, suggesting that the initial observations on PDA were not artifacts. Similarly, the identical endophytic habit of this bacterium was established from roots of kernels germinated in soil. The presence of the bacterium only, between cells and in young, healthy-appearing, developing seedling roots suggests that this relationship is not detrimental and is not interpreted as a stage in the decomposition of root from the surface inwards. The results are shown below in Tables 1–4.

The data indicate that the endophytic nature of B. subtilis RRC 101 is established very early during germination and is based on the occurrence of bacterial cell within the aleurone layer of cells and the germination scar produced early during germination must have served as the infection port. Further, the data suggest that the radicle and coleoptile are first colonized and from these initial points of infection, the bacterium spreads internally. The initial infection of these embryonic organs, which depending on the biocontrol traits (Wilson et al, Plant Dis., Vol. 69, 375–378, 1985) of this isolate, may not reflect secondary and nodal root colonization. However early radicle root colonization was reported as being a prerequisite for subsequent colonization of secondary roots by bacteria in wheat (Weller et al, Phytopathology, Vol. 73, 463–469, 1983) which correlates with the present isolation of B. subtilis not only from secondary roots but also from surface sterilized leaves. The mode of entry of the bacterium into the coleoptile and radicle has not been established. In the root, only a few cells of the epidermis were slightly damaged, possibly during fixation, suggesting that generalized autolytic degeneration is probably not involved in the colonization process.

One strain of E. cloacae, EcCt-501, is used for biological control, as described above, but the precise mechanism is unknown. This enteric bacterium has been characterized by a number of morphological and biochemical traits which allow it to be an efficient biocontrol organism. An important morphological trait is the presence of Type I fimbriae that may be important in colonizing plant roots (Nelson et al, Phytopathology, Vol. 76, 327–335, 1986). These fimbriae are inducible (Ewing, supra) and were absent in the isolate of the present invention under conditions which allow it to endophytically colonize corn seedling roots. Other biochemical traits that have been considered in the mode of action for the bacterium include reduced stimulated metabolism by plants (Nelson, Plant Soil, Vol. 129, 61–73, 1990), the production of ammonia (Howell et al, Phytopathology, Vol. 78, 1075–1078, 1988), and siderophore production (Costa et al, Mol. Plant-Microbe Interact., Vol. 4, 440–448, 1994), none of which has yet been determined for strain RRC 101. Strain RRC 101 also differs by the production of antibiotic.

TABLE 1

Effects of B. subtilis and F. moniliforme on the root and shoot growth of two cultivars of corn.

| Treatment | 6 day-old seedlings | |
| --- | --- | --- |
| | Primary root† | Shoot height |

| Cultivar 1 | | | |
| --- | --- | --- | --- |
| Silver Queen | Control | 15.4 | 5.2 |
| | Ent* | 16.8 | 6.6 |
| | Ent 26ss | 14.5 | 5.8 |
| | Ent 24wf | 15.2 | 5.8 |
| | FM 374 | 12.1 | 5.8 |
| Cultivar 2 | | | |
| Reid yellow dent | Control | 13.0 | 5.5 |
| | Ent | 15.4 | 6.4 |
| | Ent 26ss | 16.1 | 7.0 |
| | Ent 24wf | 11.4 | 3.7 |
| | FM 374 | 7.2 | 4.7 |

†Numbers represent average length or height in centimeters for 24 seedlings per cultivar per treatment except for FM374 seedlings where the numbers represent 8 seedlings per cultivar per treatment.
*Ent, Bacillus subtilis; Ent26ss and Ent24wf are rifampicin mutants; FM374, F. moniliforme 374.

TABLE 2

Effects of *Bacillus subtilis* and *Fusarium moniliforme* RRC374 on 3 week-old corn seedlings.

| Cultivar | Treatment | Seedling height | Leaf width |
|---|---|---|---|
| Silver Queen | Control | 43† | 1.0 |
| Silver Queen | B. subtilis | 57 | 2.0 |
| Silver Queen | FM 374* | 32 | 1.0 |
| Reid yellow dent | Control | 44 | 2.0 |
| Reid yellow dent | B. subtilis | 51 | 2.0 |
| Reid yellow dent | FM 374 | 25 | 1.0 |
| Reid yellow dent | Ent & FM 374 | 49 | 2.0 |

†Numbers represent average seedling height or leaf width in centimeters for three seedlings per treatment per cultivar.
*FM, *F. moniliforme*, and ENT, *Bacillus subtilis*.

TABLE 3

Distribution of *Bacillus subtilis* within plant parts of corn grown for a total of 16 weeks.*

| Week | Blade | Sheath | Stem | Cob | Kernel |
|---|---|---|---|---|---|
| 8 | $1 \times 10^1$ | $1 \times 10^2$ | $1 \times 10^2$ | — | — |
| 12 | $1 \times 10^2$ | $1 \times 10^1$ | $1 \times 10^3$ | $1 \times 10^1$ | — |
| 16 | $1 \times 10^1$ | $1 \times 10^1$ | $1 \times 10^3$ | $1 \times 10^1$ | — |

*Roots were positive ($1 \times 10^{3-4}$) from weeks 1 through 16.

TABLE 4

Total distribution of *Bacillus subtilis* within corn plants grown within a greenhouse.

| Week | CFU/g dry wt. |
|---|---|
| 1 | $1 \times 10^2$ |
| 2 | $1 \times 10^2$ |
| 3 | $1 \times 10^1$ |
| 4 | $1 \times 10^3$ |
| 8 | $1 \times 10^3$ |
| 12** | $1 \times 10^2$ |
| 16** | $1 \times 10^2$ |

**The plants were setting seed during these weeks.

EXAMPLE 5

Temperature Effects on Colonization of Seedlings

To determine the effects of soil temperatures on the colonization of corn seedlings by *Bacillus subtilis*, both RRC 101 and rifampicin mutants of the bacterium were used. The rifampicin mutants were also used as a marker insuring that the bacterium that is added is the one recovered. All seeds were double sterilized, as in Example 1 above, to insure that all internal and external microorganisms were removed. Sterilized kernels were inoculated with about $10^3$ to about $10^9$ CFU of *B. subtilis* RRC 101 and its mutants. The kernels were air dried for 12–24 hour periods and the kernels planted in sterilized soil contained in either 2 or 4 inch plastic pots. Pots of soil were placed in incubators under either 25° C., 15° C., 10° C. or 40° C. Germination was followed and all germinated plants were surfaced sterilized with full-strength CLOROX (5.25% Sodium hypochlorite) for 10–15 minutes, portions of leaves, stems, or roots aseptically removed and plated out on nutrient agar with or without rifampicin. For ease in presentation, the number of cells (CFU, colony forming units per gram dry weight) in all plant parts were combined. The results are shown below in Table 5. Most of the kernels incubated at 10° C. and 4° C. germinated. However they produced only coleoptiles and embryonic roots. Germination times varied such that data does not reflect similar harvest time.

TABLE 5

Colonization of *Bacillus subtilis* in seedlings or embryonic tissue of corn kernels incubated at cool temperatures[a].

| | Growth temperature cfu* | | | |
|---|---|---|---|---|
| B. subtilis | 25 C. | 15 C. | 10 C. | 4 C. |
| wild type | $10^6$ | $10^2$ | $10^2$ | $10^1$ |
| rifampicin mutant | $10^5$ | $10^3$ | $10^2$ | 10 |

[a]Most of the kernels incubated at 10 and 4 C. germinated, producing only coleoptiles and embryonic roots; germination times varied such that data did not reflect similar harvest time.
*Cfu, colony forming units per gram dry weight.

EXAMPLE 6

Inoculation of Seeds Known to be Toxic to Horses

A 12–24 hour *B. subtilis* RRC 101 inoculum is prepared in nutrient broth. The cells are harvested by centrifugation at 20,000 G for 15 minutes and the broth is poured off. The cells are resuspended in distilled water to produce a final concentration within the range of about 103 to about 109 cells per milliliter. This aqueous solution is sprayed onto corn kernels which are toxic to horses and contain large amounts of the fumonisin mycotoxin. The kernels are considered to be naturally infected and toxic. Also included were seed-grade and seed-grade corn, which served as controls. The kernels are allowed to dry overnight at room temperature. The seeds were planted in sterilized soil and grown at 50° F. for thirty days as described above in example 5. The results are shown below in Table 6. It can be seen that in the presence of the bacterium, kernel germination and total herbage yield was significantly increased.

TABLE 6

Effects of *Bacillus subtilis* on the germination and growth of corn naturally infected with *Fusarium moniliforme*

| Sample type | Fungal density (cfu)[a] | % Germination[b] | | Total herbage yield[c] | |
|---|---|---|---|---|---|
| | | — | ++ | — | ++ |
| 1 | $3 \times 10^9$ | 52 | 75 | 41 | 114 |
| 2 | $3 \times 10^7$ | 43 | 90 | 19 | 93 |
| Seed grade | $1 \times 10^2$ | 98 | 99 | 86 | 147 |
| Feed grade | $1 \times 10^3$ | 81 | 93 | 93 | 135 |

[a]Numbers represent both external and internal *F. moniliforme* count (other fungi, 30–40%).
[b]Germination determined after 30 days; +, or −, bacterium added or not added.
[c]Determined after 30 days growth (g dry wt).

EXAMPLE 6

Interaction of *Fusarium moniliforme* and *Bacillus subtilis* in Two Soil Types

Antagonism between *B. subtilis* RRC 101 and fungus is shown in the soil. Either both *F. moniliforme* and *B. subtilis* RRC 101, or each alone, are grown for 14 days in autoclaved moist Cecil sandy clay (Georgia type soil) or synthetic soil mix obtained from commercial sources at 25° C. starting at an inoculum density of $10 \times 10^2$ cfu per gram of soil for each microorganism. The results are shown below in Table 7. The data show that in the presence of the bacterium, *F. moniliforme* is prevented from growing in the soil.

TABLE 7

Interaction of *Fusarium moniliforme* and *Bacillus subtilis* in two soil types*

| Soil type | *Fusarium moniliforme* | *Bacillus subtilis* | Fusarium & Bacillus |
|---|---|---|---|
| Cecil sandy clay | $6.9 \times 10^{12}$ | $4.9 \times 10^5$ | $3.4 \times 10^3 / 5.3 \times 10^9$ |
| Synthetic | $12.0 \times 10^{15}$ | $17.0 \times 10^4$ | $2.5 \times 10^2 / 8.1 \times 10^5$ |

*Grown for 14 days in autoclaved moist (45%) soil at 25 C.; starting inoculum density of each was $10 \times 10^2$ cfu per gram of soil.

EXAMPLE 7

Spontaneous Rifampicin-Resistant Mutant of RRC 101

Resistance to the antibiotic rifampicin is rare among soil and plant bacteria. The chromosomal nature of the mutation affords greater stability than occurs with plasmid-borne markers, and it is not easily transferable. Thus, mutations to this antibiotic can be used to study the ecological success of parent types in live soils and in the in planta situation.

Spontaneous rifampicin-resistant mutant strains from *Bacillus subtilis* RRC 101 were isolated on nutrient agar containing 100 microgram of rifampicin per ml. A solution of cells, $10^4$/ml, was spread on the rifampicin medium and colonies picked; the isolation frequency was $10^{-8}$. The rifampicin ($RIF^R$) mutations were stable without reversion to wild types after more than 30 passages in nutrient broths, as well as sterile soil. The mutants selected were given the designation of RRC ENT24WF and ENT2655 and they were maintained on nutrient agar containing 50 microgram of rifampicin at 4° C., or on silica gel as described for the parental type RRC 101.

$RIF^R$ mutation was identical to the parent strain with the noted exception of producing a more pronounced inhibitory effect on the growth of *F. moniliforme* and other fungi when cultured in vitro. The zone of inhibition observed in FIG. 5, for example, was 3 to 4 times wider for *Fusarium moniliforme*, and for other fungi growth was completely inhibited. This $RIF^R$ mutation is capable of infecting corn kernels and no decreased symbiotic effectiveness was noted. Growth rate in vitro is identical to the parent strain and this mutation is easily culturable on media and soil types containing sufficiently high concentrations of *Fusarium moniliforme*. *Bacillus subtilis* RRC ENT24WF is superior to the ecological fitness of the parent types, based on its in vitro effects against fungi (see for example Tables 1, 5, and 8).

EXAMPLE 8

Interaction of Soil Types with *Bacillus subtilis* and *Fusarium moniliforme* on Seed Germination

*B. subtilis* RRC 101 and two rifampicin mutants of it, Ent24wf and Ent26ss, were used in a study in sand or a synthetic soil mix (3B-Mix). Two different corn types were used and included the sweet corn, Silver Queen, and a field corn, Reid Yellow Dent, The kernels of these cultivars were double sterilized and inoculated as described above in Examples 1 and 2. Per cent germination was determined after 14 days. The results are shown below in Table 8. The data, in addition to indicating that there is increased germination when the bacterium or its mutants are applied to kernels, also show that in the presence of the fungus, germination is reduced. Thus, mutants of this bacterium can be used as markers.

The foregoing detailed description is for the purpose of illustration. Such detail is solely for that purpose and those skilled in the art can make variations therein without departing from the spirit an scope of the invention.

TABLE 8

Interaction of soil types with *Bacillus subtilis* and *Fusarium moniliforme* on seed germination.

| | | % Germination | | | | |
|---|---|---|---|---|---|---|
| Cultivar | Soil type | Control | Ent* | Ent24wf | Ent26ss | Fungus |
| Silver queen | sand | 95a | 96a | 100a | 92a | 65b |
| Reid Yellow Dent | sand | 90a | 95a | 85a | 80a | 45b |
| Silver Queen | 3B-mix | 98a | 100a | 100a | 95a | 31b |
| Reid Yellow Dent | 3B-mix | 93a | 93a | 90a | 90a | 60b |

*Ent, *Bacillus subtilis*, Ent24wf, and Ent26ss are rifampicin mutants; and fungus is *F. moniliforme* RRC374. Soil mix 3B-mix is a commercial synthetic soil mix.
**Means within a row followed by the same letter are not different by LDS at $P \leq 0.05$.

We claim:

1. A bacteria-containing agricultural inoculum suitable for inoculating plant seeds comprising
    (a) an endophytic symbiotic *Bacillus subtilis* selected from the group consisting of ATCC 55732, a rifampicin-resistant strain of ATCC 55732, and mixtures thereof, wherein said strain is an endophytic symbiont in plants and suppresses growth of plant pathogenic fungi, and
    (b) a suitable carrier that is non-phytotoxic, non-bacteriostatic, and non-bacteriocidal.

2. A composition of matter comprising a plant seed inoculated with an isolated strain of a plant endophytic symbiotic *Bacillus subtilis* selected from the group consisting of ATCC 55732, a rifampicin-resistant strain of ATCC 55732, and mixtures thereof, wherein said strain suppresses growth of plant pathogenic fungi.

3. A *Bacillus subtilis* selected from the group consisting of ATCC 55732, a rifampicin-resistant strain of ATCC 55732, and mixtures thereof, wherein said strain is an endophytic symbiont in plants and suppresses growth of plant pathogenic fungi.

4. A method of protecting a plant from disease caused by a plant pathogenic fungus comprising inoculating seeds from said plant with a symbiotic endophytic strain of *Bacillus subtilis* selected from the group consisting of ATCC 55732, a rifampicin-resistant strain of ATCC 55732, and mixtures thereof, wherein said strain is an endophytic symbiont in plants and suppresses growth of plant pathogenic fungi.

5. A plant colonized with an isolated culture of an endophytic symbiotic stain of *Bacillus subtilis* selected from the group consisting of ATCC 55732, a rifampicin-resistant strain of ATCC 55732, and mixtures thereof, wherein said strain is an endophytic symbiont in plants and suppresses growth of plant pathogenic fungi.

\* \* \* \* \*